(12) United States Patent
Karmali

(10) Patent No.: US 6,184,227 B1
(45) Date of Patent: Feb. 6, 2001

(54) SALTS OF AMINOIMIDAZOLE CARBOXAMIDE USEFUL IN THE PREVENTION AND TREATMENT OF LIVER DISEASES

(75) Inventor: Rashida A. Karmali, New York, NY (US)

(73) Assignee: SavviPharm Inc., New York, NY (US)

( * ) Notice: Under 35 U.S.C. 154(b), the term of this patent shall be extended for 0 days.

(21) Appl. No.: 09/295,639

(22) Filed: Apr. 20, 1999

Related U.S. Application Data

(63) Continuation-in-part of application No. 09/231,147, filed on Jan. 15, 1999, which is a continuation-in-part of application No. 08/966,066, filed on Nov. 10, 1997, now Pat. No. 5,912,346, which is a continuation-in-part of application No. 08/684,297, filed on Jul. 18, 1996, now Pat. No. 5,861,406, which is a continuation-in-part of application No. 08/505,439, filed on Jul. 21, 1995, now Pat. No. 5,728,707.

(51) Int. Cl.$^7$ ............... A61K 31/4166; A61K 31/506
(52) U.S. Cl. ............................... 514/274; 514/386
(58) Field of Search ................... 544/310; 548/326.5; 514/274, 386

(56) References Cited

U.S. PATENT DOCUMENTS

| | | | |
|---|---|---|---|
| 3,271,398 | 9/1966 | Haraoka | 260/256.4 |
| 5,728,707 | * 3/1998 | Wehrmann | 514/274 |
| 5,861,406 | * 1/1999 | Wehrmann | 514/274 |
| 5,912,346 | * 6/1999 | Wehrmann | 514/310 |

OTHER PUBLICATIONS

J.S. Flier, et al New Engl J. Med. 333: 1058–1065, 1995.
R. Murphy et al., Ann Intern Med 113: 799–802, 1990.
N. Aarsaether et al., Biochim Biophys Acta, 958: 70–80, 1988.
B.A. Lauterberg J Hepatol, 7: 384–390, 1988.
P.M. Hall, Hepatology 14:906–910, 1991.
R.D. Situnayake et al, Gut 31:1311–1317, 1990.
G. Erkstrom, Biochem Pharmacol 38: 1313–1319, 1989.
H.e. Driver, et al., Anticancer Res 7:309–320, 1988.

* cited by examiner

Primary Examiner—Richard L. Raymond

(57) ABSTRACT

Compositions and methods are described for the prevention and treatment of tissue damage caused by alcohol, therapeutically helpful drugs as well as industrial, dietary and environmental toxins, using an effective amount of salts of aminoimidazole carboxamide.

20 Claims, 14 Drawing Sheets

Figure 1:
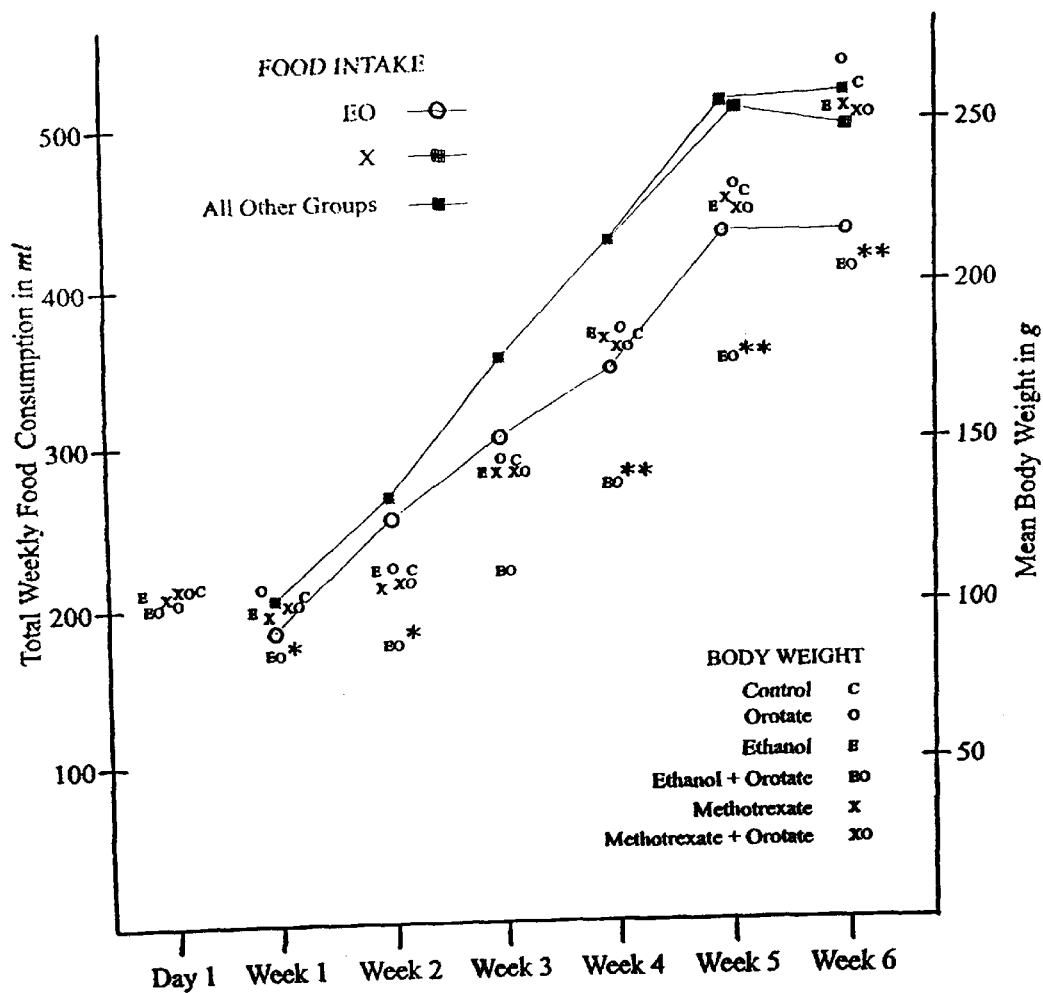

SALTS OF AMINOIMIDAZOLE CARBOXAMIDE USEFUL IN THE PREVENTION AND TREATMENT OF LIVER DISEASES

This application is a continuation-in-part of U.S. patent application Ser. No. 09/231,147, filed Jan. 15, 1999, which is a continuation-in-part of U.S. application Ser. No. 08/966,066, filed Nov. 10, 1997, issued as U.S. Pat. No. 5,912,346, which is a continuation-in-part of U.S. application Ser. No. 08/684,297, filed Jul. 18, 1996, issued as U.S. Pat. No. 5,861,406, which is a continuation-in-part of U.S. application Ser. No. 08/505,439, filed Jul. 21, 1995, now U.S. Pat. No. 5,728,707.

1. INTRODUCTION

The present invention is directed to methods and compositions for the prevention and/or inhibition of tissue injury caused by alcohol, therapeutically useful drugs as well as by industrial, dietary and environmental toxins, by administration of salts of aminoimidazole carboxamide (AICA). Use of the entire group of organic acid salts and inorganic acid salts of 5-aminoimidazole carboxamide rather than only those obtained from orotic acid are encompassed by the methods of the invention. For example, AICA may also be reacted with aliphatic acids including, but not limited to, lactic, succinic, maleic, citric, and tartaric or with sugar acids such as gluconic, galactonic, etc., particularly penta and poly hydroxycarboxylic acids to form organic acid salts, or AICA may be reacted with inorganic acids including, but not limited to, hydrohloric and phosphoric acids, to form inorganic salts suitable for use according to the methods of the present invention.

The methods involve administering to an individual consuming alcohol, therapeutic drugs and/or exposed to xenobiotic agents, an effective dose of a salt of aminoimidazole carboxamide with or without antioxidants, including, but not limited to vitamin E, vitamin C, vitamin A and its derivatives, glutathione, N-acetylcysteine or magnesium gluconate. In the practice of the invention, compositions containing salts of AICA are used to detoxify harmful and noxious agents or toxins, to inhibit bioactivation of agents to harmful electrophiles or free radicals, to inhibit suppression of cell-mediated or humoral immune mechanisms, to stimulate the regeneration of target cells of the damaged issue and to inhibit the failure of energy supply. Preferred compositions of the invention are those which specifically or preferentially inhibit tissue injury involving , but not limited to, hepatocytes, nonparenclymal cells, endothelial cells, pit cells and other cells lining the hepatic sinusoids and bile duets.

2. BACKGROUND OF THE INVENTION

2.1 Salts of Aminoimidazole Carboxamide

AICA orotate, also referred to as "Orazamide Orotate" is incorporated into animal nucleic acids and possesses the ability to prevent necrosis of liver induced by acute and chronic hepatic damage in animals. Miller, C. S. et al., 1950, Science 112: 654.

2.1.1 Chemical Nature and Properties of Salts of Aminoimidazole Carboxamide

Orazamide is available in different forms as: 5-aminoimidazole-4-carboxamide orotate, 4-amino-5-imidazole carboxamide orotate or a combination of 1,2,3,6-tetrahydro-2,6-dioxo-4-pyrimidine carboxylic acid with 5-amino-1H-imidazole-4-carboxamide (1:1) or a combination of orotic acid with 5(or 4)-aminoimidazole-4(or 5)-carboxamide (1:1). The C5 amine group on the imidazole ring can be attached to the C4 carboxyl group of orotic acid or any other organic acid which is chemically compatible to the body:

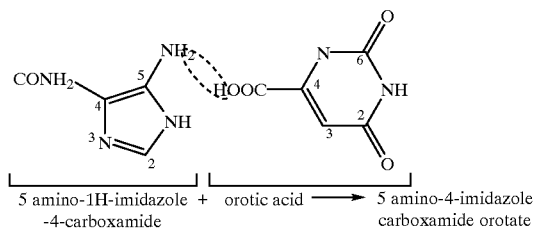

5 amino-1H-imidazole + orotic acid ⟶ 5 amino-4-imidazole
-4-carboxamide                                     carboxamide orotate

2.1.2 Metabolic Effect of Orotic Acid

Any kind of organic or inorganic acid which is clinically compatible with the body may be selected to be reacted with AICA, an intermediate in the purine pathway. Especially desirable are orotic, lactic, succinic, maleic, citric, tartaric, gluconic, galactonic, hydrochloric, phosphoric and penta or poly hydroxycarboxylic acids.

Orotic acid is an intermediate in the pyrimidine pathway and its main source in human and animal diet is bovine milk and its products.

2.2 Alcohol and Liver Disease

An association of alcohol with damage to the liver rests primarily on the clinical observation that cirrhosis occurs in-patients consuming large amounts of ethanol. Ethanol has been shown to have a variety of toxic effects on livers in otherwise normal animals, including normal men and women.

Alcohol abuse costs the U.S. more than one hundred and sixteen billion dollars per year, of which about twelve percent is for direct costs of medical care. Advertising, counter advertising and depiction in the public media, 1986, JAMA 256: 1485. The basic reason for the large epidemic of alcohol-related disease is that ethanol is an effective drug in relieving anxiety, depression and the pressures of modern society. The easy availability of ethanol and the social acceptability of ethanol consumption are advertised widely and aggressively. The public seems unaware that chronic use of ethanol in the absence of addiction can lead to serious medical illness and/or the development of social consequences. About three quarters of the population of the United States uses ethanol. The incidence of alcoholism in the United States is approximately seven percent, being higher for men (11 percent) than for women (4.08 percent). Alcohol Health and Research World, 1995, 18: 243–8.

Prevention and/or treatment of alcoholism is a problem for which there are no certain answers. Therefore, an understanding of the biochemical basis for the hepatotoxicity of ethanol and its eventual control may provide an effective means to reduce and manage alcohol related liver diseases and medical complications.

2.3 Therapeutic Drugs and Liver Disease

Drug-induced liver disease is encountered rarely in general practice but accounts for between two to three percent of all admissions due to adverse drug reactions. Lewis, J. H., et al., 1989, Med. Clin. North Am. 73: 775. Published compilations of drug-related liver pathology list between 500 and 1000 therapeutic agents that have been implicated in the etiology of various liver diseases. Zimmerman, H. J., 1990, Semin. Liver. Dis. 10: 322.

Drugs with the potential for producing liver injury are divided into the "direct" or "predictable" hepatotoxins and "unpredictable" hepatotoxins. Direct hepatotoxins produce liver damage in a predictable, dose-dependent fashion, and they produce liver cell necrosis that affects predominantly a particular region of the liver lobule. Unpredictable hepatotoxins produce liver injury that is diffuse, consisting of necrosis and/or cholestasis, usually associated with a significant inflammatory reaction. Despite significant advances in the understanding of hepatotoxicity, the mechanisms by which certain drugs injure or kill the liver cell, or alter its function remain largely unknown and uncontrolled.

2.4 Industrial and Environmental Toxins and Liver Disease

The liver's potential for injury by environmental or occupational/industrial toxins is very high because it is the first organ after the gastrointestinal tract that is exposed to these agents, also known as xenobiotics. Hepatic metabolism usually detoxifies these agents. However, hepatic metabolism of xenobiotics can result in metabolites that are considerably more hepatotoxic than the parent chemicals. The hepatotoxic effects that result in humans from accidental or intentional exposures to xenobiotics or toxins range from mild liver dysfunction to necrosis. Xenobiotics may react with nutrients, destroy them or make them unavailable because of altered absorption or changes in detoxification or metabolic rates. Nutritional deficiencies in turn may enhance the toxic effects of xenobiotics. The realization that commonly used chemical compounds present health hazards has stirred considerable apprehension not only for industrial workers exposed directly to these agents but also for the general public who unwittingly get exposed to these ubiquitous noxious agents in the environment, in the food they eat or in their homes.

3. SUMMARY OF THE INVENTION

The present invention is directed to a method for the prevention and treatment of tissue damage caused by alcohol which involves administering a salt of AICA to an individual in need thereof.

The present invention is also directed to a method for the prevention and treatment of drug-induced liver disease which involves administering a salt of AICA to an individual in need thereof.

The present invention further involves a method for the prevention and treatment of hepatotoxic effects of exposure to xenobiotics and/or toxins, which involves administering a salt of AICA to an individual in need thereof.

The present invention is also directed to a method of inhibiting the oxidation of ethanol and toxic effects of acetaldelyde, a toxic and reactive intermediate in ethanol oxidation, by administering a salt of AICA to an individual in need thereof.

The present invention is also directed to a method of inhibiting the conversion of therapeutic drugs to reactive metabolites such as electrophiles or free radicals, by administering a salt of AICA to an individual in need thereof.

The present invention is also directed to a method of detoxifying hepatotoxic xenobiotics into harmless metabolites or inhibiting the conversion of xenobiotics into metabolites that are considerably more hepatotoxic than the parent chemicals, by administering a salt of AICA to an individual in need thereof.

The present invention is also directed to a method for preventing suppression of cellular and hormonal immunity caused by alcohol, therapeutic drugs and xenobiotics, which involves administering an effective dose of an AICA salt to an individual in need thereof.

The present invention is also directed to a method for inducing the regeneration of liver cells, which involves administering an effective dose of an AICA salt to an individual in need thereof.

The present invention is also directed to a method for the prevention and treatment of liver damage caused by alcohol which involves administering a salt of AICA and an antioxidant selected from the group consisting of vitamin E, vitamin C, vitamin A and its derivatives, glutathione, N-acetylcysteine and magnesium gluconate, to an individual in need thereof.

The present invention is also directed to a method for the prevention and treatment of liver damage caused by alcohol which involves administering a salt of AICA and an inhibitor of aldehyde dehydrogenase selected from the group consisting of disulfiram, pargyline, reserpine and sulfonylureas.

The present invention is also directed to a method for the prevention and treatment of drug-induced liver disease which involves administering a salt of AICA and an antioxidant selected from the group consisting of vitamin E, vitamin C, vitamin A and its derivatives, glutathione, N-acetylcysteine and magnesium gluconate to an individual in need thereof.

The present invention further involves a method for the prevention and treatment of hepatotoxic effects of xenobiotics and/or toxins, which involves administering a salt of AICA and an antioxidant selected from the group consisting of vitamin E, vitamin C, glutathione, N-acetylcysteine and magnesium gluconate to an individual in need thereof.

4. BRIEF DESCRIPTION OF THE DRAWINGS

For a fuller understanding of the invention, reference is had to the following description taken in connection with the accompanying figures, in which:

FIG. 1 demonstrates interaction of ethanol methotrexate, and orazamide orotate on weekly total food consumption and mean body weights expressed as totals or means. Statistical analysis was carried out by: a) Kruskal-Wallis ANOVA on Ranks ($p<0.05$ vs. orazamide orotate *); and b) by 2-way ANOVA with SNK post-hoc test ($p.<0.05$ vs. all others **).

Figure 2:
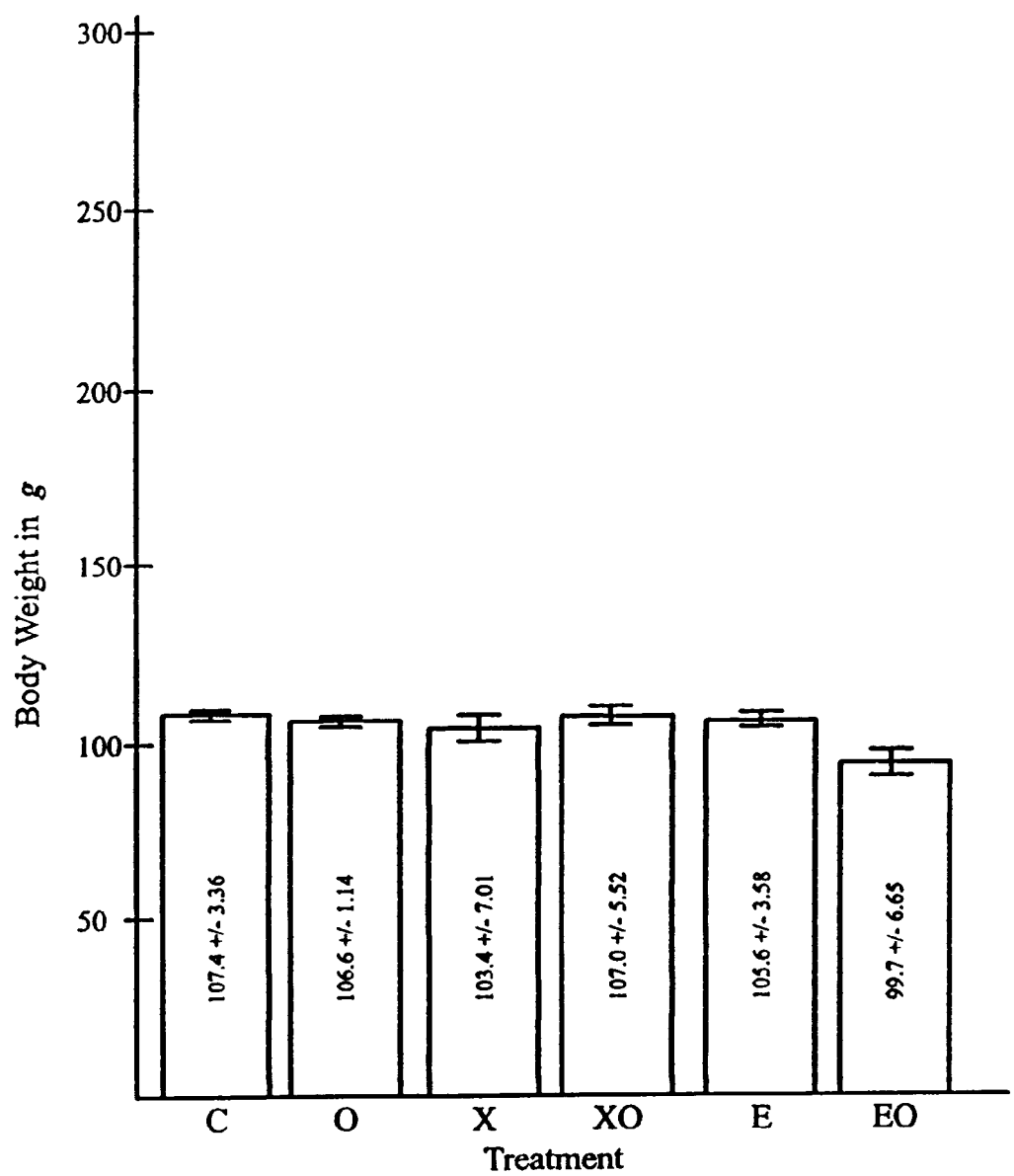

FIG. 2 demonstrates initial body weights (data expressed as mean +/−SD). No significant differences were obsessed by 2-way ANOVA.

Figure 3:
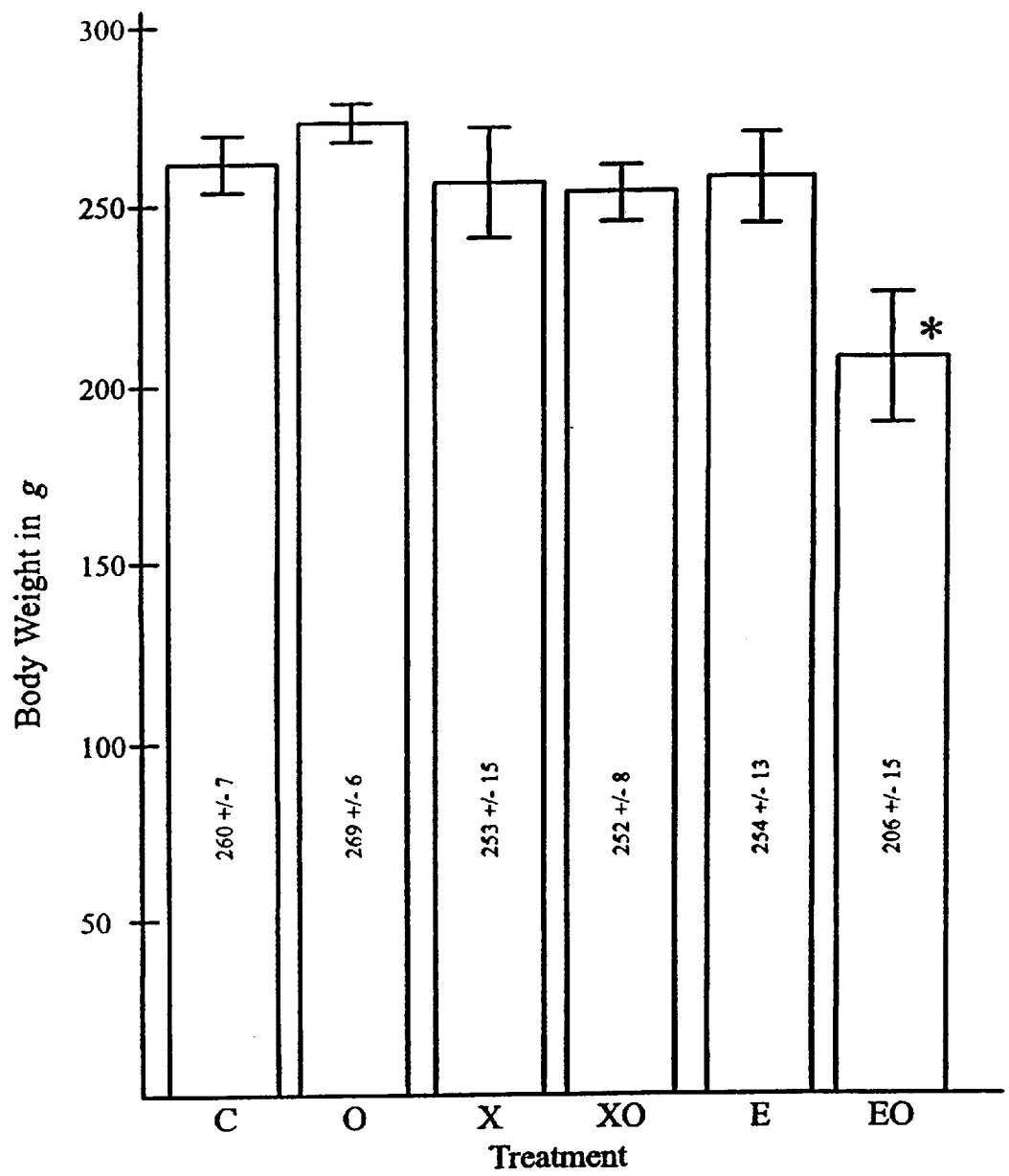

FIG. 3 demonstrates results of a six-week treatment with ethanol, methotrexate and orazamide orotate on body weight (expressed as mean +/−SD). The statistical significance expressed as * was $p.<0.05$, tested by 2-way ANOVA with SNK post-hoc test.

Figure 4:
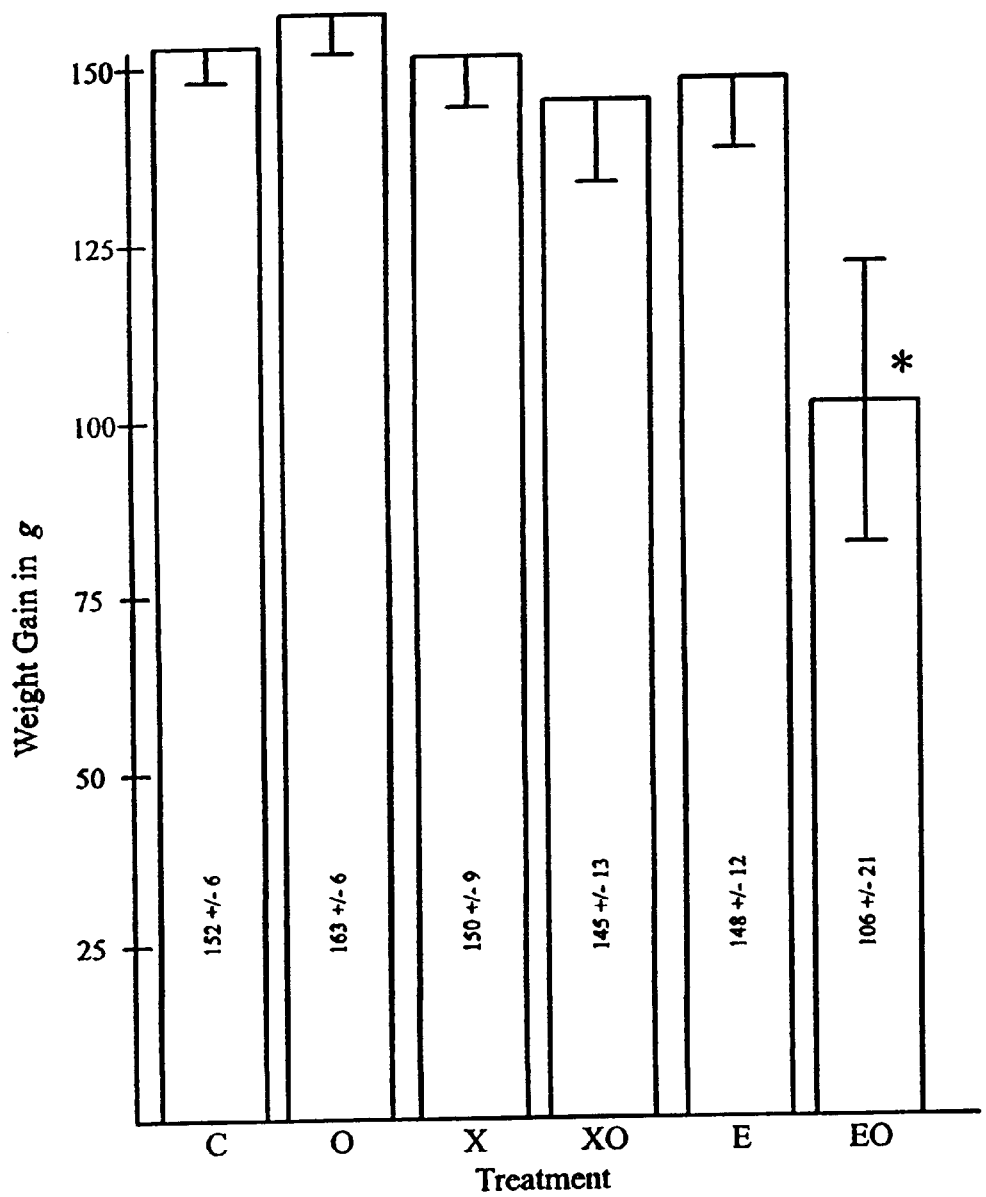

FIG. 4 demonstrates results of a six-week treatment with ethanol, methotrexate and orazamide orotate on weight gain (expressed as mean +/−SD). * $p.<0.05$ by 2-way ANOVA with SNK post-hoc test.

Figure 5:
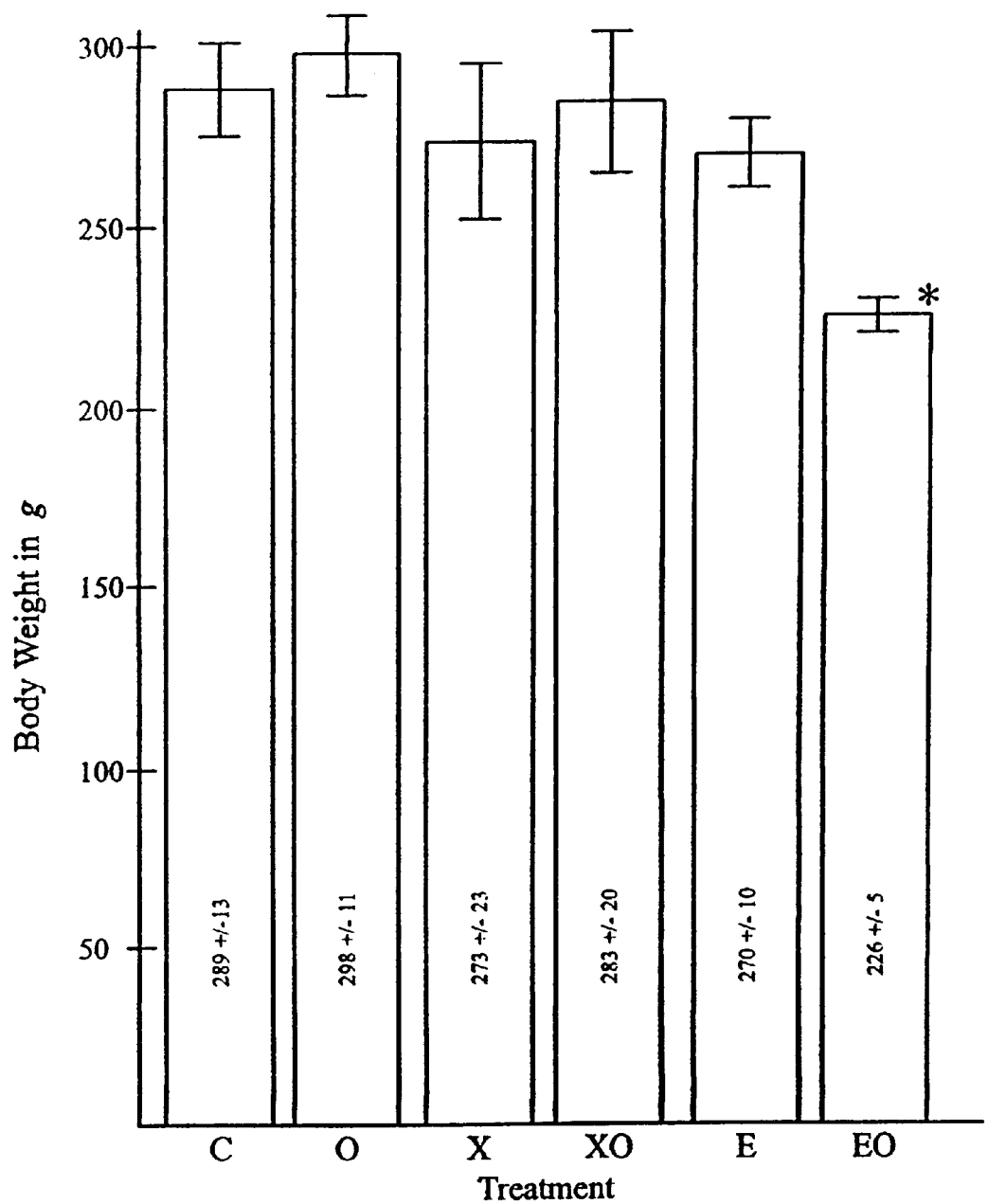

FIG. 5 demonstrates interaction of ethanol, methotrexate and orazamide orotate on final body weights (expressed as mean +/−SD). * $p.<0.05$ vs. C & O by Kruskal-Wallis ANOVA Ranks.

Figure 6:
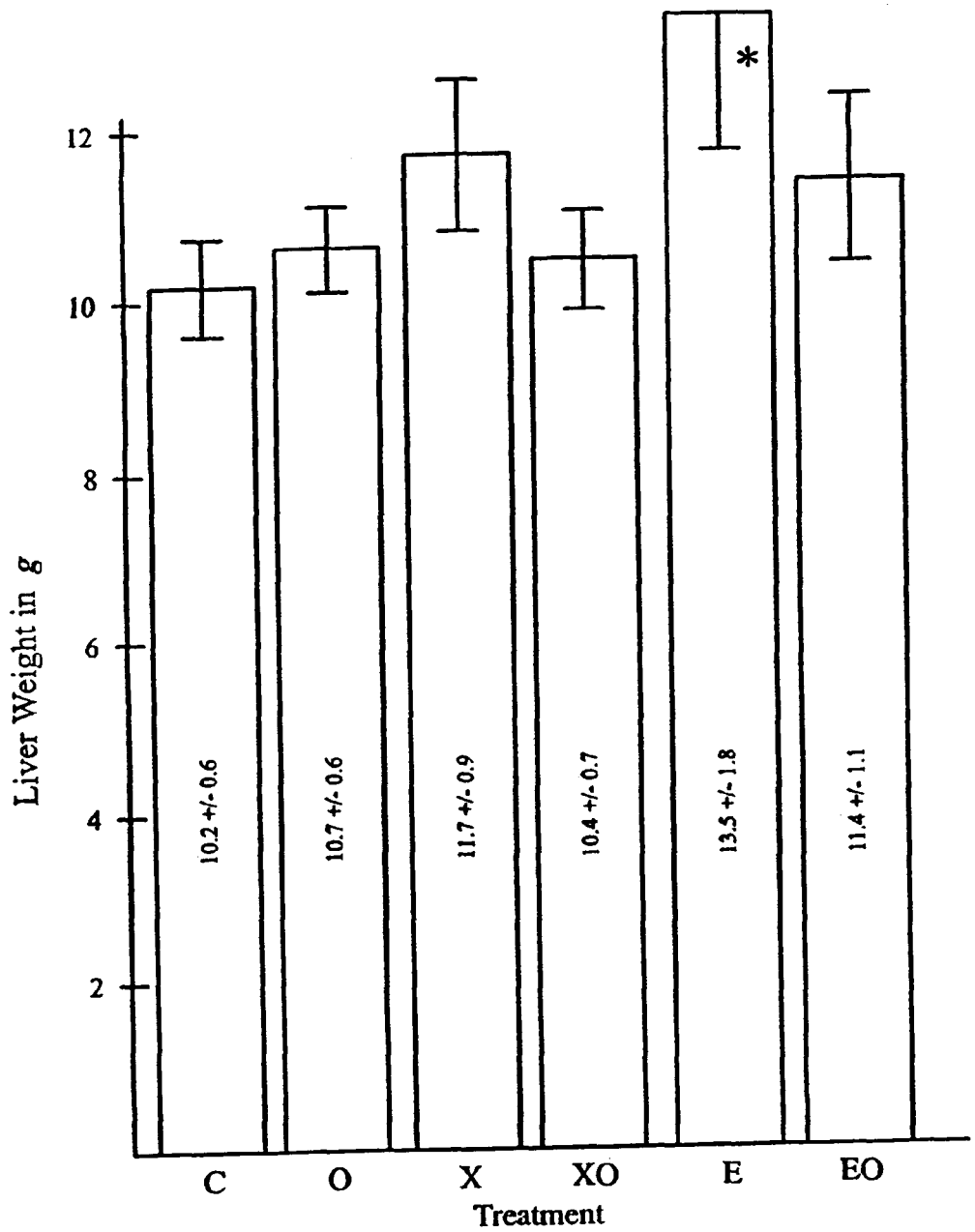

FIG. 6 demonstrates interaction of ethanol, methotrexate and orazamide orotate on final liver weights (expressed as mean +/−SD). * $p.<0.05$ vs. all others; 2-way ANOVA with SNK post-hoc test.

Figure 7:
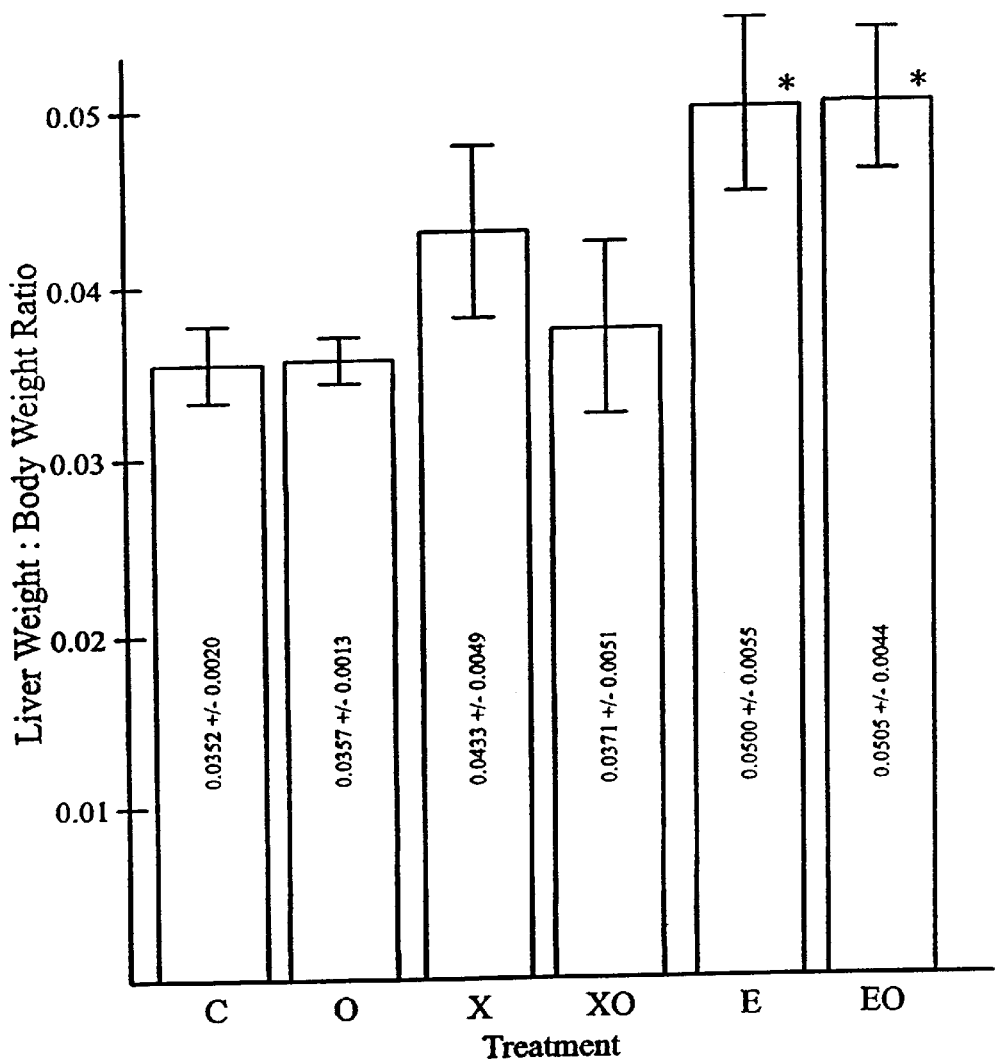

FIG. 7 demonstrates interaction of ethanol, methotrexate and orazamide orotate on liver weight; body weight ratios (expressed as mean +/−SD). * $p.<0.05$ vs. C; Kruskal-Wallis ANOVA on Ranks.

Figure 8:
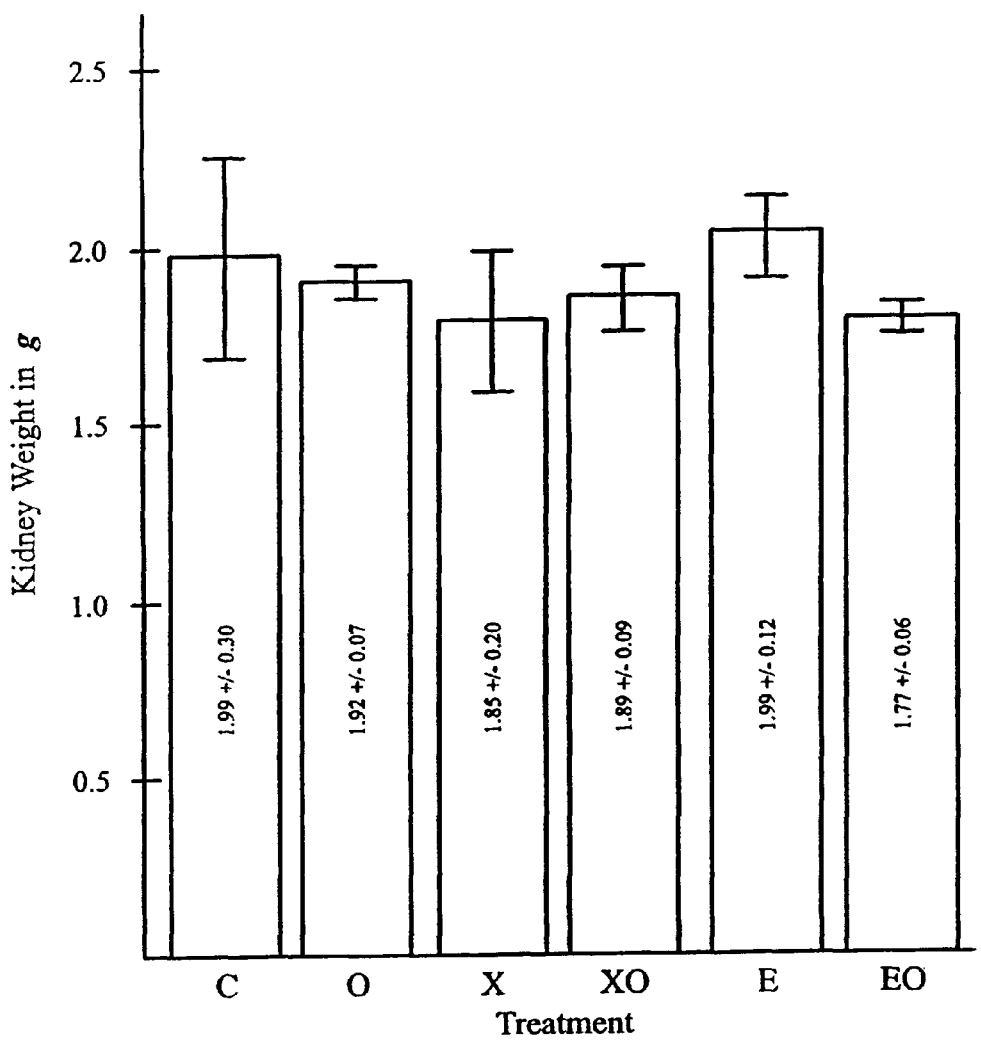

FIG. 8 demonstrates interaction of ethanol, methotrexate and orazamide orotate on final kidney (right and left) weight (expressed as mean +/−SD.) No statistical difference between treatments.

Figure 9:
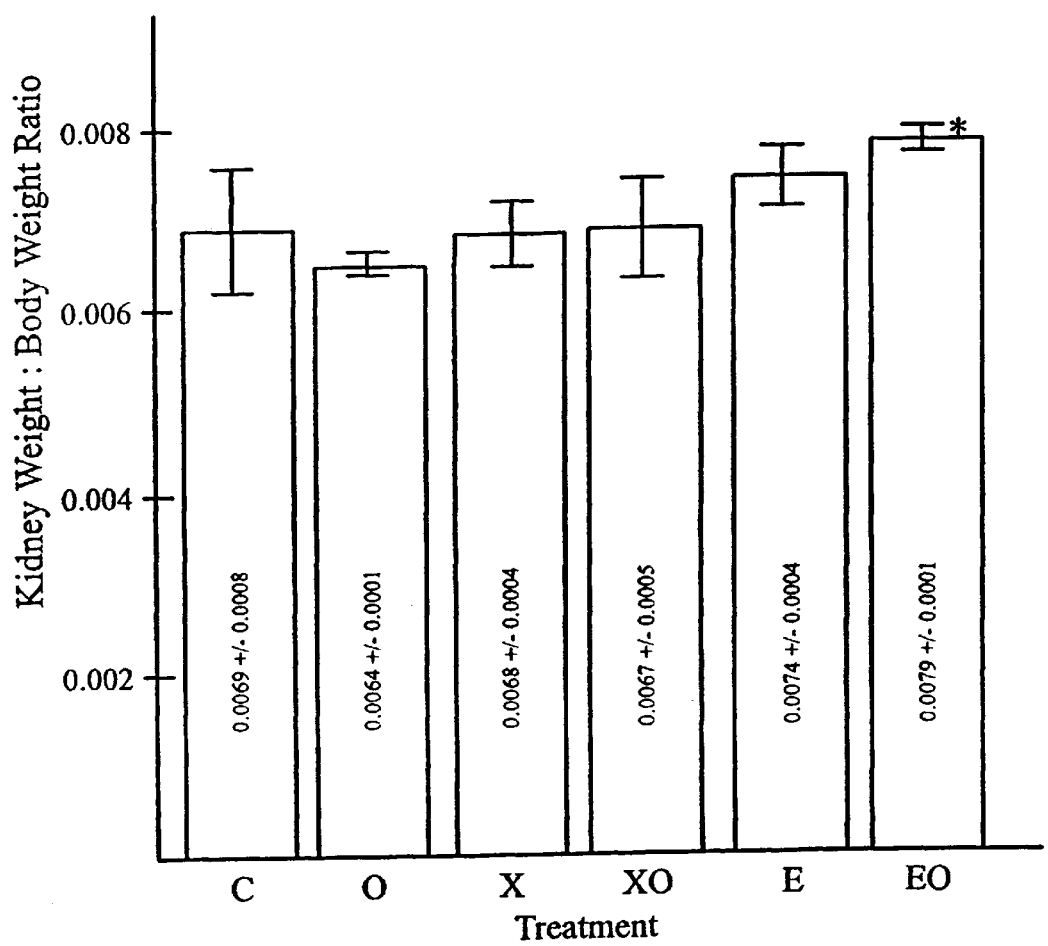

FIG. 9 demonstrates interaction of ethanol, methotrexate and orazamide orotate on kidney weight: body weight ratios (expressed as mean +/−SD). * p.<0.05 vs. O; Kruskal-Wallis on Ranks.

Figure 10:
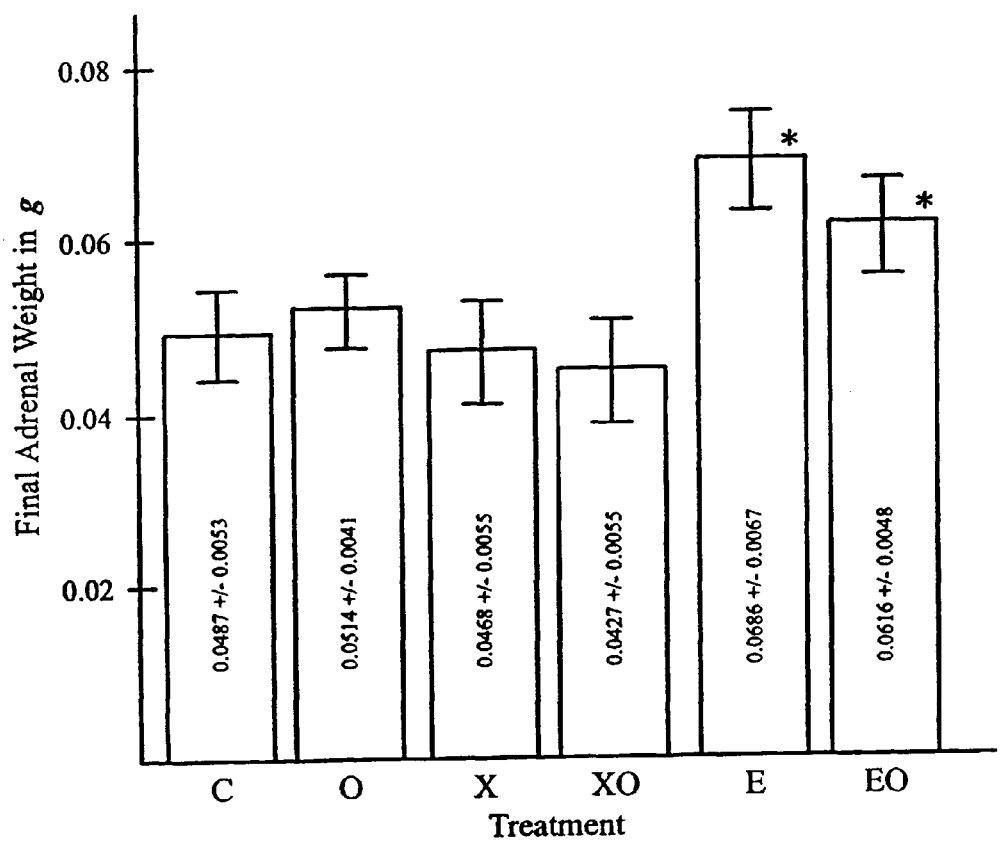

FIG. 10 demonstrates interaction of ethanol, methotrexate and orazamide orotate on final adrenal weights (expressed as mean +/−SD). * p.<0.05 vs. C, O, X and XO;; 2-way ANOVA with SNK post-hoc test.

Figure 11:
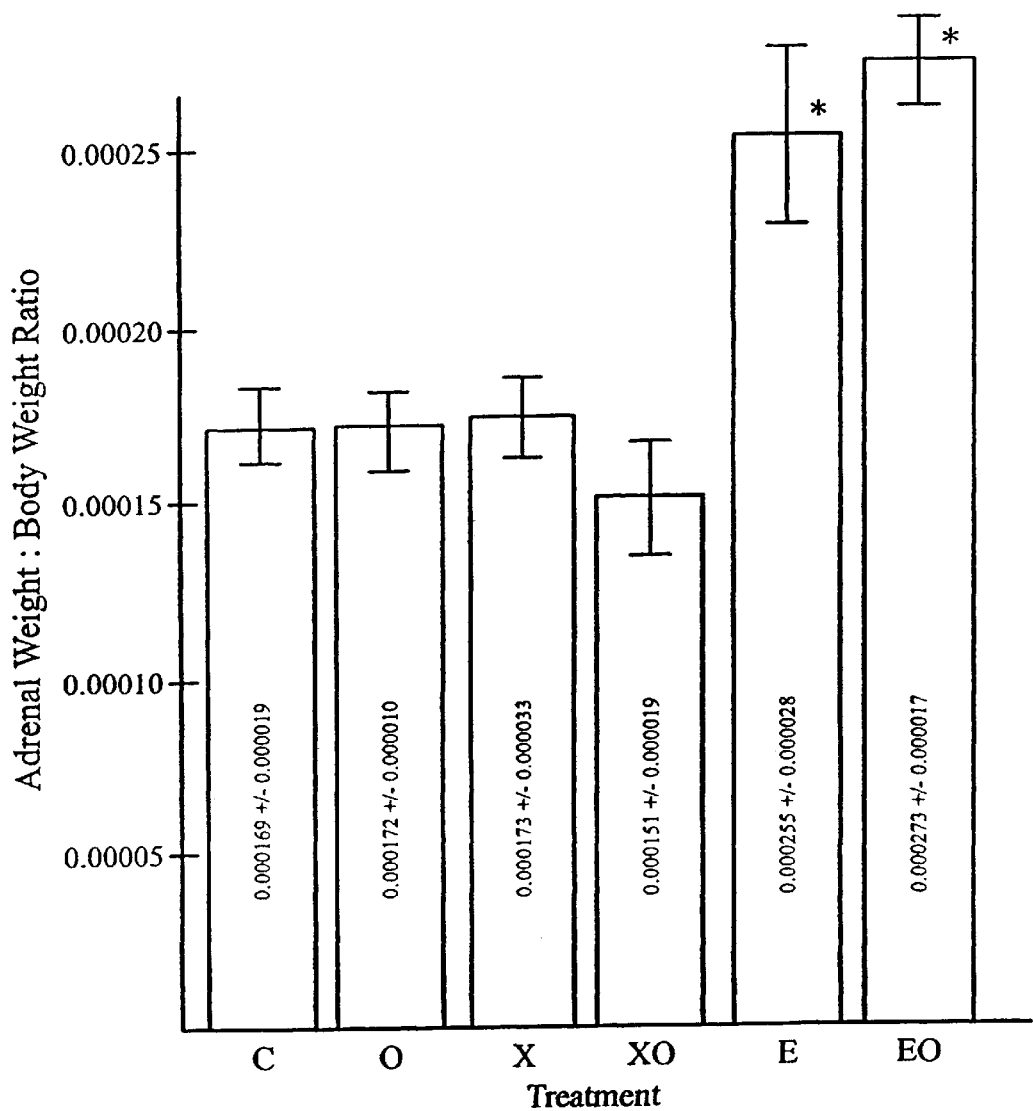

FIG. 11 demonstrates interaction of ethanol, methotrexate and orazamide orotate on adrenal weight (expressed as mean +/−SD). * p.<0.05 vs. C, O, X, and XO; 2-way ANOVA with SNK post-hoc test.

Figure 12:
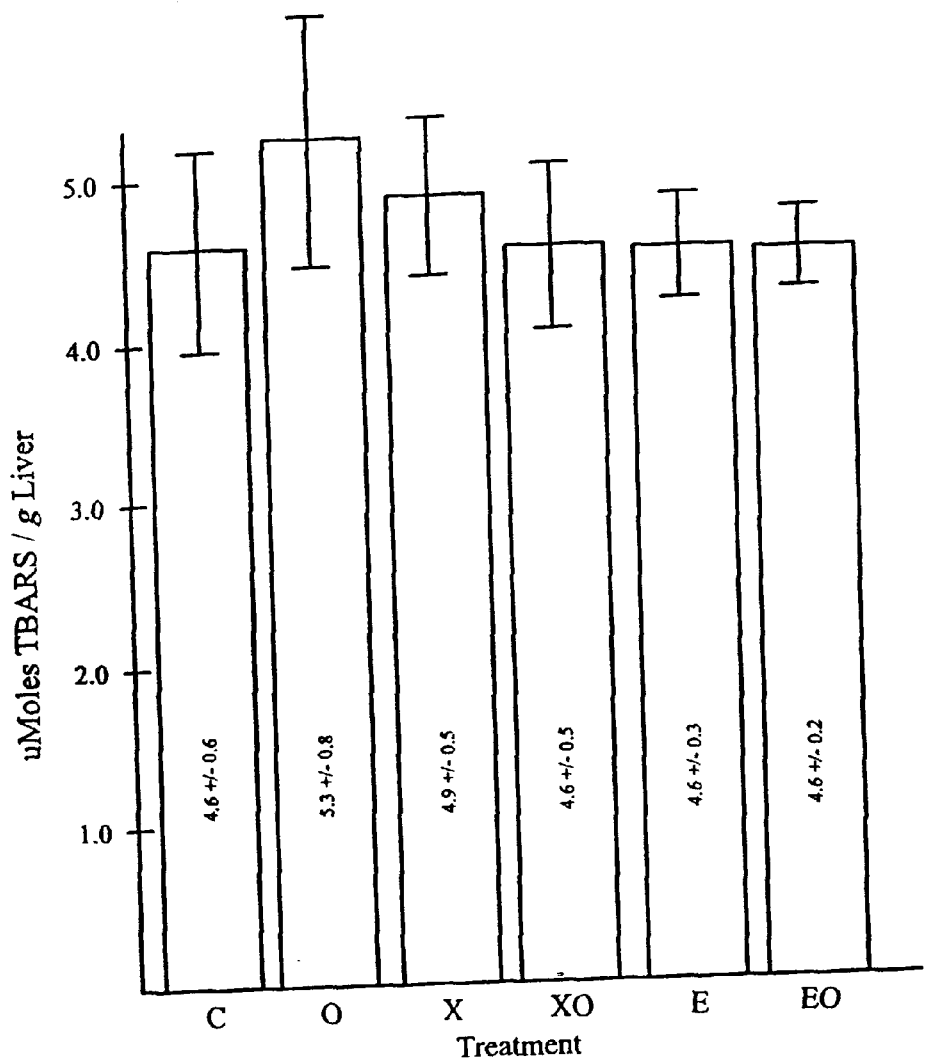

FIG. 12 demonstrates interaction of ethanol, methotrexate and orazamide orotate on TBARS in liver (expressed as mean +/−SD). No statistical significant differences.

Figure 13:
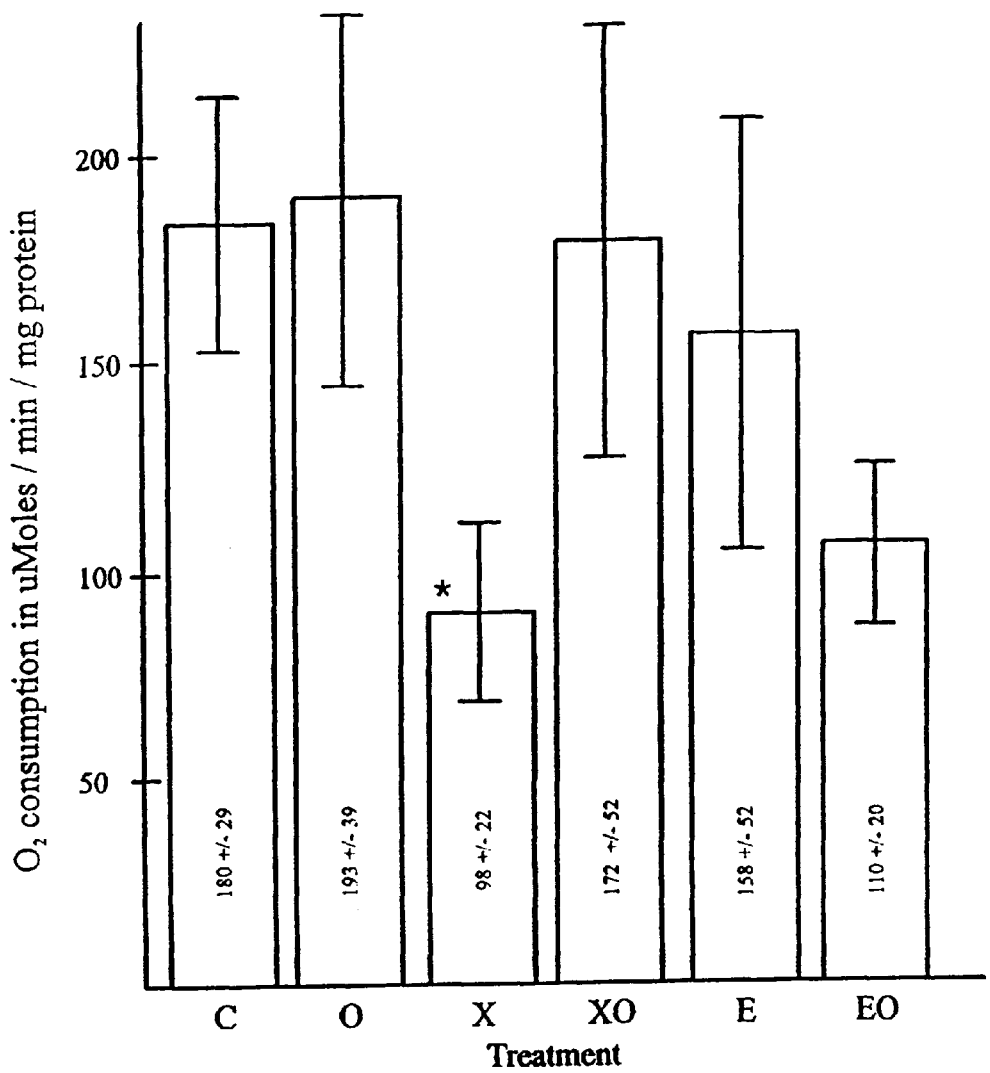

FIG. 13 demonstrates interaction of ethanol, methotrexate and orazamide orotate on oxygen consumption by liver mitochondria incubated with succinate, cytochrome C and Triton X100. Results indicate the number of electron transport chains (expressed as mean +/−SD). * p.<0.05 (E+EO) vs. (C+O); p.<0.05 vs. (X+X)) vs. (C+O); p.<0.05 vs. O, C. B, XO, 2-way ANOVA.

Figure 14:
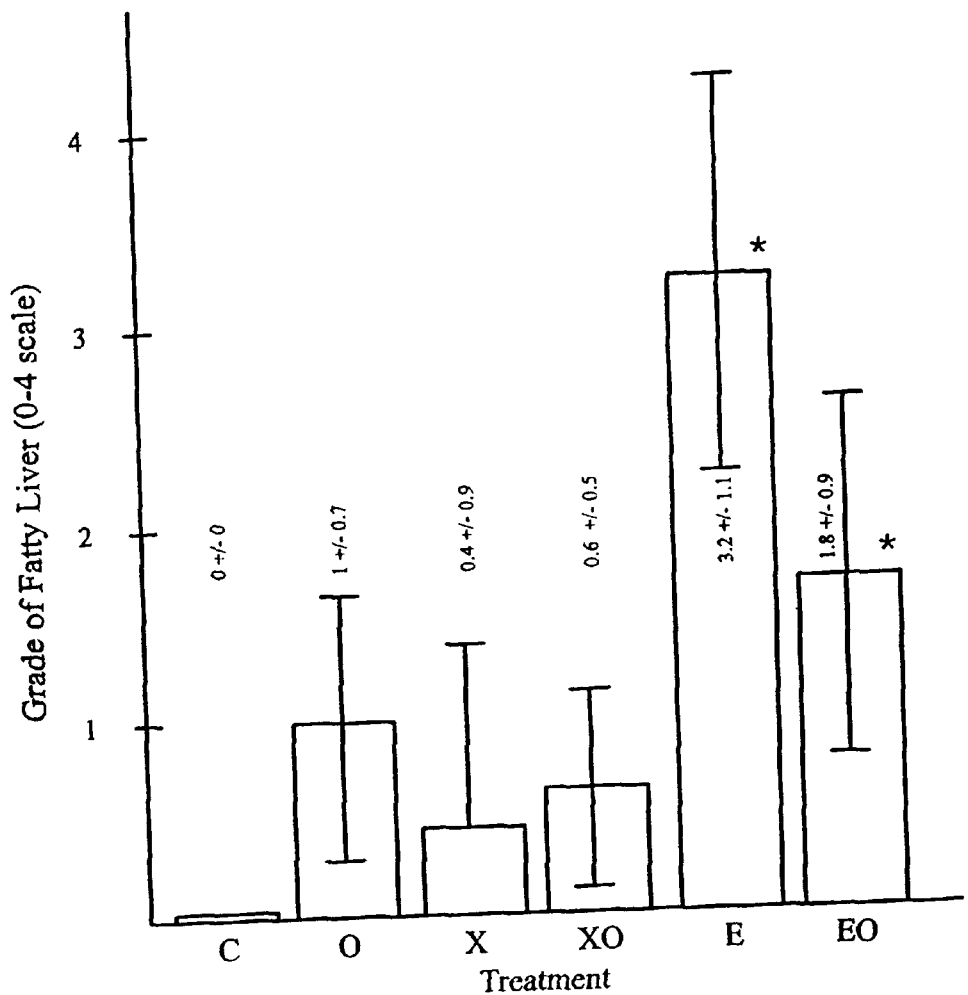

FIG. 14 demonstrates interaction of ethanol, methotrexate and orazamide orotate on fatty infiltration in liver (expressed as mean +/−SD). * p.<0.05 vs. C; Kruskal-Wallis ANOVA on Ranks.

5. DETAILED DESCRIPTION OF THE INVENTION

The method of the invention involves administering an effective dose of an inorganic acid salt or organic acid salt of AICA to an individual using alcohol and/or therapeutically useful drugs or one who is exposed to industrial, dietary and environmental toxins, in order to prevent and/or inhibit liver injury caused by these agents.

It will be apparent to those skilled in the art that other salts of AICA or agents having antioxidant properties and inhibit liver injury and enhance liver cell regeneration, may be useful as therapeutic agents. Such additional compounds may be identified using liver cell injury assays described herein.

It may be that the ability of AICA salts alone or in combination with antioxidants, to detoxify harmful and noxious agents, to inhibit bioactivation of agents to harmful electrophiles or free radicals, to inhibit suppression of cell-mediated or humoral immune mechanisms, to stimulate the regeneration of liver cells and/or to inhibit failure of energy supply, contribute to the efficacy or effectiveness for use in the prevention and treatment of liver injury caused by alcohol, therapeutically useful drugs as well as industrial and environmental toxins. These possible mechanisms of action are in no way meant to limit the scope of the invention and are presented purely for explanatory and/or illustrative purposes.

5.1 Metabolism of Alcohol and Mechanism of Liver Injury

Alcohol cannot be stored and ninety to ninety-five percent of ingested ethanol is metabolized in the body to acetaldelyde and to acetate. The remainder is excreted intact via the lungs and kidneys and in sweat. Oxidation of ethanol in the liver accounts for nearly all ethanol metabolism and small amounts are oxidized in kidneys, muscles, intestines and lungs. The healthy individual cannot metabolize more than 160–180 g/day.

Ethanol oxidation is catalyzed by enzymes within the cytosol of the liver cell and by enzymes that are attached to the endoplasmic reticulum. The conversion of ethanol to acetaldellyde takes place in the cytosol and is catabolized by alcohol dehydrogenase (ADH).

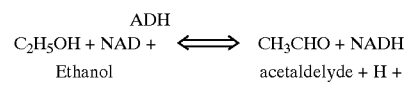

Acetaldelyde in mitochondria and cytosol may be injurious, causing membrane damage and cell necrosis. The acetaldelyde is converted to acetate by aldehyde dehydrogenase (ALDH).

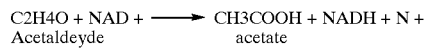

Acetate may be oxidized to carbon dioxide and water or converted by the citric acid cycle to other biochemically important compounds including fatty acids. NAD is a co-factor and hydrogen acceptor when alcohol is converted to aldehyde and further to acetate. The NADH generated shuttles into the mitochondria and changes the NADH:NAD ratio and redox state of the liver. The hydrogen generated replaces fatty acid as a fuel and is followed by triglyceride accumulation and fatty liver. The redox state of the liver changes, protein synthesis is inhibited and lipid peroxidation increases. Situnayake, R. D. et al., 1990, Gut 31:1311.

The marked increase in the NADH:NAD ratio in oxidizing alcohol results in lactic acidosis, ketosis, collagen formation, altered steroid metabolism and impaired gluconeogenesis.

Acetaldehyde is a key factor in the hepatic injury caused by ethanol. Acetaldehyde binds to proteins, lipids and DNA to form stable and unstable adducts, which damage key functions of the cells. Some adducts behave an "neoantigens" and stimulate an immune response and an immune-mediated injury. Acetaldehyde can promote oxidative stress by reacting with and depleting cellular glutathione, an endogenous free radical scavenger. Lauterberg, B. H. and Bilzer, M., 1988, J. Hepatol 7:384 and Bloor, J. H., et al., 1994, Adv. Intern. Med 39:49.

Impaired humoral immunity in alcoholic liver disease is shown by elevations of serum immunoglobin levels and deposition of IgA. Impaired cell-mediated hepatic injury is shown by antibodies reacting with ethanol-altered liver cell membrane antigens. Neuberger, J., et al., 1984, Gut 25:300.

10–15% of alcohol is metabolized by a microsomal p450 ethanol oxidizing system (MEOS). P450-II-E1 is part of this system and is inducible by alcohol and by some drugs such a acetaminophen and xenobiotics. Lieber, C. S., 1995, N. Engl. J. Med. 333:1058. This accounts for the susceptibility of the alcoholic to drugs that are hepatotoxic and which, when given in therapeutic doses, can cause serious liver injury. Induction of P450-II-E1 increases oxygen consumption, acetaldehyde production and promotes lipid peroxidation. During microsomal peroxidation, injurious reactive oxygen radicals or free radicals are produced and initiate lipid peroxidation. Metabolism of ethanol requires an excess supply of oxygen, a requirement that is met through proliferation of endoplasmic reticulum and induction of MEOS. The activity of MEOS favors utilization of reduced nucleotides. An excess of reducing equivalents results in generation of reactive oxygen species.

The amount and type of fat in the diet is a key determinant in producing the lesions seen in alcoholic liver disease.

Saturated fat is relatively protective against development of alcoholic liver diseases and poly unsaturated fatty acids are linked with more severe liver injury. Nanji, A. A. and French, S. W., 1986, Alcoholism Clin Exp Res. 10;217; and French, S. W., 1993, Alcohol 23:97.

In rats fed corn oil plus ethanol, the progression of liver injury was accompanied by a decline in the production of prostaglandin E2 (PGE2) and prostacyclin (PGI2), and an increase in production of leukotriene B (LTB4) and thromboxane B2 (TXB2) by nonparenclymal liver cells. With continued alcohol feeding, the ratio of eicosanoids shifts away from PGE2 and PGI2 to TXB2. This is because the level of lipid peroxides in liver cells alters the activity of the enzymes of the arachidonic acid cascade and increases the synthesis of TXB2. Nanji, A. A., et al. 1994, Life Sci. 55:611; and Nanji, A. A., et al., 1994, Mol. Cell Biochem. 140:85.

The mechanisms by which thromboxane may cause liver injury are unknown but may involve TXA2-induced vasoconstriction and hypoxia, bleb formation in isolated hepatocytes and inflammation. Horton, A. A. and Wood, J. M., 1990, Biochem. Biophys. Acta. 319:1022; and Goldman, G., et al., 1991, Cir. Res. 68:1013.

Therefore, an intervention aimed at inhibiting the production of lipid peroxides and related free radical moieties, for example, TXA2, can be expected to exert a protective effect against alcohol-induced liver injury. Thromboxane A2 synthesis can be inhibited by imidazole compounds, for example, aminoimidazole carboxamide. Horrobin, D. F., et al., 1978, Med. Hypothesis 4:178–184; and Terano, S., et al., 1985, Adv. Prost. Thromb. Leuk Res. 15–315. In addition, AICA was found to have antioxidant activity and to increase superoxide dismutase activity. Muzces, G., et al., 1990, Acta Physiologica Hungaria 76:183–190.

In the present invention administration of salts of AICA results in inhibition of thromboxane A2, enhanced antioxidant defenses against lipid peroxides and free radicals and increased nucleotide synthesis. More specifically, administration of AICA orotate results in prevention and/or inhibition of alcohol induced-liver injury and regeneration of damaged liver tissue. AICA salts in combination with antioxidants in the present invention are also useful for the prevention and treatment of alcohol-induced liver injury.

5.2 Drug-Induced Liver Disease

The liver is particularly concerned with drug metabolism and drugs which are avidly taken up by the liver are said to have a high first-pass metabolism. The hepatic clearance of drugs given by mouth depends on the efficiency of the drug metabolizing enzymes, the intrinsic clearance, the liver blood flow and the extent of plasma protein binding.

The main drug-metabolizing system resides in the microsomal fraction of the liver cell smooth endoplasmic reticulum. The enzymes concerned are mixed function mono-oxygenases, cytochrome, c-reducatse and cytochrome P450. Reduced NADPH in the cytosol is a co-factor.

Enzyme inducers include barbiturates, alcohol, anaesthetics, hypoglycaemic and anticonvulsant agents, griseofulvin, rifampicin, glutethimide, phenylbutazone and meprobamate. Enlargement of the liver following drug therapy can be related to enzyme induction.

Drug metabolism and the production of toxic metabolities is performed by the P450 system of haemoproteins situated in the endoplasmic reticulum of the hepatocyte. At least 50 P450s have been identified and three families are concerned with drug metabolism—P450-I, P450-II, and P450-III. Most direct hepatotoxins that produce liver cell injury require activation to reactive metabolites via cytochrome P450 enzymes. Table 1 describes some characteristics of human liver P450s. Watkins, P. B., 1990, Simin. Liver Dis. 10;235.

| P450 | Drug Substrate | Probable Inducer |
|---|---|---|
| 1-A2 | Caffeine<br>Theophylline | Cigarette smoke<br>Ace Taminophen |
| 11-C | Diazepam<br>Phenylbutazone<br>Tolbutamide | |
| 11-D | Most beta-blockers<br>Most neuroleptics<br>Codeine | |
| 11-E1 | Acetaminophen<br>Ethanol | Ethanol<br>Isoniazid |
| 111 | Cyclosporin A<br>Erythromycin<br>Ketoconazole<br>Nifedipine<br>Oestrogen S<br>Lidocaine | Anti-seizure medications<br>Rifampicin<br>Glucocorticoids |

Since ethanol induces P450-II-E1, it also enhances the toxicity of acetaminophen and aspirin. Similarly, patients treated with isoniazid which also induces P450-II-E1 have increased acetaminophen toxicity. Murphy, P., et al., 1990, Ann Intern. Med. 113:799.

Like acetaminophen, asprin is a well-documented cause of a dose-related, reversible form of hepatotoxicity. Of the currently available non-steroidal anti-inflammatory drugs (NSAIDS) in the United States, diclofenac, sulindac, and phenylbutazone appear to carry the greatest risk of liver toxicity; piroxicam, ibuprofen, naproxen and fenoprofen carry and intermediate risk. Tolman, K. G., 1990, J. Rheumatol. (Suppl.) 22:6.

The reactive metabolites produced by P450 enzymes, often electrophiles or free radicals, form covalent adducts with proteins, lipids and nucleic acids, leading to disruption of their function. Oxidative processes also appear to be of fundamental importance in the pathogenesis of cell damage. Lipid peroxidation is prominent in several types of drug induced hepatic injury. Electrophilic conjugates also complex with intracellular antioxidants such as glutathione and deplete their supply. Oxidant stress causes mitochondrial injury and leads to impairment of cellular energy production and adenosine triphosphate (ATP) depletion and eventually to toxic liver injury. Mehendale H M et al., 1994, FASE J 8:1285.

As discussed supra, in Section 5.1, intervention with AICA salts alone or in combination with antioxidants results in increased blood flow by inhibiting TXA2-induced vasoconstriction, and inhibition of lipid peroxide and free radical production. More specifically, use of AICA orotate in the present invention results in prevention and/or inhibition of drug-induced liver toxicity, regeneration of damaged liver tissue, renewal of nucleotides and energy supply.

5.3 Liver Disease Caused by Industrial and Environmental Toxins

The liver's potential for injury by ingested chemicals, toxins or elements is very high because it is the first organ after the gastrointestinal tract that is exposed to these agents. Hepatic metabolism usually detoxifies these agents. Hepatic metabolism of chemicals however, can result in metabolites that are considerably more hepatotoxic than the parent chemicals. The response of the liver to a toxin is determined by a variety of factors such as dose, duration of exposure, route of exposure, age of the individual, simultaneous exposure to other drugs or toxins, the presence or lack of established liver disease, and the inherent sensitivity of the exposed individual to the noxious agent.

The realization that common and frequently used chemical compounds present carcinogenic hazards has raised serious concerns not only for industrial workers exposed directly to these agents but also for the general public who get exposed to these agents in the environment, in the food and in their food and in their homes.

A variety of classifications has been used to group hepatotoxins according to the clinical symptoms they produce—acute, subacute or chronic hepatitis, or according to the mechanism by which they produce their hepatotoxicity.

Consumption of alcohol increases the risk of human cancers of the upper respiratory and digestive tracts and liver, cancer of the stomach, large bowel, pancreas, lung, urinary tract and breast. Several lines of evidence suggest that a mechanism of action may be augmentation of the tumorigenic effects of genotoxicants by ethanol and/or other constituents of alcoholic beverages. There is a synergism between usage of alcohol and of tobacco, know to contain a wide selection of genotoxicants, in contribution to human risk of cancers of the upper respiratory and digestive tracts and liver. Driver, H. E., and Swann, P. F., 1987, Anticancer Res. 7:309.

Table 2 describes some important chemicals and their application and hepatotoxicity. Pond, S.M. et al., 1982, West J. Med. 137:509.

| CHEMICAL | USES | HEPATIC RESPONSES |
| --- | --- | --- |
| Arsenic and inorganic salts | In production of dyes, ceramics, drugs, paint, ink, petroleum and semiconductors | Acute injury and death of parenchymal cells; cirrhosis; angiosarcoma |
| Beryllium | Alloys, cathode ray tubes, electrical equipment, gasmantles | Granulomata |
| Carbon Tetrachloride | Degreasers, fat processors, fire extinguisher, fumigant, insecticides, refrigerants, propellants, rubber and wax | Acute injury and death of parenchymal cells, cirrhosis, carcinoma |
| Dioxane | Solvent, degreaser, cement component, adhesives, deodorants, detergents, emulsions, fats, glue, lacquer, oil, paint, polish, shoe cream, varish remover, waxes | Subacute injury of parenchymal cells |
| Phosphorus (yellow) | Pyrotechnics, explosives, fertilizers, rodenticides, semiconductors | Acute injury and death of parenchymal cells. |
| Polychlorinated biphenyls | Cable insulation, dyes, electrical equipment, herbicides, lacquers, paper treatment, plasticizers, resins, rubber textiles | Subacute injury of parenchymal cells |
| Tetrachloro-ethane | Drycleaning agent, fumigant, solvent, degreases, gaskets, lacquers, paints, resins, varnish, wax | Acute injury and death of parenchymal cells. |
| Tetrachloro-ethylene | Solvent, degreasers, chemical intermediate, fumigant, gums, rubber, soap, vacuum tubes, wax | Acute injury and death of parenchymal cells. |
| Vinyl Chloride | Chemical intermediate and solvent; in production of polyvinyl chloride and resins | Fibrosis, cirrhosis, angiosarcoma, carcinoma. |

Carbon tetrachloride is an example of a potent hepatotoxin and its toxicity is largely dependent on the metabolic transformation of the parent compound into a toxic metabolite by mixed-function oxidase enzyme of the liver. The toxicity is related to the dose, age, species and sex of the animal exposed. Substances known to stimulate hepatic cytochrome P450, such as barbiturates and alcohol, potentate the hepatotoxicity of carbon tetrachloride. The mechanism of hepatic injury produced involves fat accumulation and necrosis.

Carbon tetrachloride is metabolized in a series of reactions by the P450 system to free radicals which cause hepatic damage by lipid peroxidation and reactions with proteins and DNA.

Other hepatotoxins include, but are not limited to, nitroaromatic compounds, nitroparaffins, mushrooms, metals (such as antimony, arsenic, lead, beryllium, cadmium, chromium, copper, phosphorus and thallium), toxic rapeseed oil, hexachlorobenzane, tannic acid, cocaine, aflatoxins, pesticides, polychlorinated biphenyls, vinyl chloride, dioxin, phthalate esters and benzyl chloride. Like carbon tetrachloride, some of these hepatotoxins or xenobiotics are metabolized into free radicals and noxious metabolites which cause reactions with proteins and DNA and ultimately liver necrosis.

As discussed supra, in Sections 5.1 and 5.2, in the present invention, AICA salts alone or in combination with antioxidants are administered to prevent and inhibit the formation of noxious metabolites and free radicals. More specifically, use of AICA orotate in the present invention results in the prevention and inhibition of drug-induced liver toxicity, regeneration of liver cells and detoxifying of industrial environmental hepatotoxins.

5.4 Choice of AICA Salt and Dosage

The present invention provides a number of different organic acid salts of aminoimidazole carboxamide which inhibit tissue injury induced by alcohol, certain therapeutic drugs or dietary or environmental toxins, e.g., 5-aminoimidazole-4-carboxamide orotate (AICA orotate) or 4-amino-5-imidazolecarboxamide orotate (AICA orotate) or a combination of 1,2,3,6-tetrahydro-2,6-dioxo-4-pyrimidine carboxylic acid compound with 5-amino-1H-imidazole-4-carboxamide (1:1) or a combination of orotic acid compound with 5(or 4)-aminoimidazole-4(or 5)-carboxamide (1:1); salts of AICA with aliphatic acids such as lactic, succinic, maleic, citric, and tartaric or with sugar acids such as gluconic, galactonic, etc., particularly penta and poly, hydroxycarboxylic acids to form organic acid salts; and inorganic acid salts such as hydrochlorides and/or phosphate salts of AICA suitable for use according to the methods of the present invention.

5.5 Dosage and Formulation

AICA salts or salts of 5-amino or substituted amino 1,2,3-triazoles may be formulated into pharmaceutical preparations for administration to mammals for inhibition of tissue injury induced by alcohol, certain drugs, and dietary or environmental toxins.

Many of the AICA or triazole salt compounds may be provided as organic acid salts with pharmaceutically compatible counterions, a form in which they are merely water-soluble. Pharmaceutically compatible salts may be formed with many acids, including, but not limited to, aliphatic acids such as lactic, succinic, maleic, citric and tartaric or with sugar acids such as gluconic, galactonic, etc., particularly penta and poly, hydroxycarboxylic acids and inorganic acids including, but not limited to hydrochloric and phosphoric acid. Salts tend to be more soluble in aqueous or other protonic solvents that are the corresponding free base forms.

The therapeutic compounds or pharmaceutical compositions may be administered intravenously, intraperitoneally, subcutaneously, intramuscularly, intrathecally, orally, rectally, topically, or by aerosol.

Formulations suitable for oral administration include liquid solutions of the active compound dissolved in diluents such as saline, water or PEG 400; capsules or tablets, each containing a predetermined amount of the active agent as solid, granules or gelatin; suspensions in an approximate medium; and emulsions.

Formulations suitable for parenteral administration include aqueous and non-aqueous isotonic sterile solutions, which contain buffers, antioxidants and preservatives. The formulations may be in unit dose or multi-dose sealed containers.

6. EXAMPLE

Orazamide Orotate Alters the Effects of Methotrexate and Ethanol on Liver

6.1 Methotrexate

Methotrexate is an antineoplastic drug which inhibits purine synthesis by inhibiting tetrahydrofolate reductase and is used in the treatment of progressive rheumatoid arthritis, cancer, and retractable psoriasis. Hall, P et al., 1991, Hepatology 14:906–910. Unfortunate side effects of methotrexate therapy include fatty liver, focal necrosis, and cirrhosis. The production of fatty liver in rat models has been reported following treatment with doses in the range of 100–125 $\mu$g/kg body weight; higher doses (200 to 500 $\mu$g/kg body weight) usually resulted in severe hepatic inflammation and necrosis resulting in death of the animal in a few weeks at the lower doses to within a couple of days at the higher doses. The low-dose model allows for a sufficiently long (6 weeks) treatment with methotrexate to induce the array of (histologic) hepatic complications observed in humans.

The mechanism of hepatic fatty infiltration is not well understood as methotrexate appears to enhance triglyceride synthesis but does not decrease lipid metabolism. Arsaether N et al., 1988, Biochim. Biophys. Acta. 958:70–80. Mitochondrial respiration (state III) is reduced by an acute dose of methotrexate. Amamoto N et al., 1989, Cell Biochem Funct. 7:129–134. However direct effects on the respiratory chain have not been observed. How these acute effects relate to chronic low dose treatment is unknown. Because methotrexate inhibits purine synthesis and ultimately, protein synthesis, the possibility exists that prolonged treatment with this antifolate will negatively affect hepatic mitochondrial function and result in sufficient dysfunction to lead to hepatic fatty liver, inflammation, necrosis, and cirrhosis.

Because low-dose methotrexate treatment over 6 weeks produces focal necrosis in some of the animals it is important to note that cellular necrosis can stimulate an inflammatory response resulting in increased synthesis of IL-1, IL-6, and TNF. These cytokines in turn stimulate the expression of the acute-phase inflammatory response elements: cyclooxygenase2 (cox2) and IL-8. Subsequent recruitment of activated neutrophils and macrophages then lead to further tissue damage and necrosis (Zhang D et al., 1995, Biochem. J. 310:143–148.), resulting in the potential for significant liver damage following prolonged treatment. A reduction in mitochondrial function could exacerbate the production of inflammatory-induced damage by reducing or preventing appropriate repair processes due to a reduced energy supply.

Chronic ethanol consumption causes fatty liver, and production of an inflammatory response in liver. The production of reactive oxygen species (ROS) secondary to ethanol-induced alterations in enzyme function may be the biochemical factor which initiates the inflammatory response. Ekstrom G et al., 1989 Biochem Pharmacol. 38:1313–1319.

6.2 Methods: The Effect of Orazamide Orotate was Tested in Rats Given Either Methotrexate or Ethanol

6.2.1 Animal Care

Sprague-Dawley rats were obtained from Holtzman Laboratory Animals (Madison, Wis.) and housed separately in stainless steel mesh-bottomed cages in an animal care facility maintained at 22° C. with a 12 hour light-dark cycle (lights on at 7:30 am). Because weight gain and organ weights were dependant variables the animals were weighed and then placed in the following groups such that each group had as close as possible to the same body weight with the same variance: Group 1=control (C); Group 2=orotate (O); Group 3=methotrexate (X); Group 4=methotrexate+orotate (XO); Group 5=ethanol (E); Group 6=ethanol+orotate (EO).

All animals were fed a "control" liquid diet on the first day of the study. The volume of food eaten by the E group (this group was fed ad libitum) was measured each day and the other animals were fed the volume of food each day that was eaten by the E group on the previous day. Because ethanol-fed animals tend to restrict their food intake the non-ethanol fed animals usually eat all of the food given to them under these conditions. This was done to make sure that nutritional and caloric differences between groups were minimal. The ethanol was progressively introduced into the liquid diets starting at 3% ethanol (w/v) for day 2, 4% for day 3 and then maintained at 5% from day 4 until the end of the study. (Five percent ethanol equates to roughly 36% of their total caloric intake).

For X treatment a 100 $\mu$g/ml solution was made up each day and sufficient X was added to the appropriate liquid diet to produce an intake equivalent to 100 $\mu$g/kg/day. For O treatment, a 10 mg/ml solution of O in dilute NaOH was made and sufficient O added to the appropriate liquid diets to produce an intake of 10 mg/kg/day.

6.2.2 Tissue Preparation and Histology

After killing by chloroform-administration the livers were removed and a 0.5 cm$^2$×0.5 cm thick portion of one lobe of liver was placed in formalin and one lobe of the liver was used to isolate mitochondria. The remainder of the liver was finely minced with scissors and then homogenized in a total of 10 volumes of Tris-buffered KCl (Ph 7.4) containing 1 mM DETAPAC and 0.1 mM BHT (to prevent artifactual formation of TBARS during the assay procedures) and TBARS and inflammatory cytokines (IL-1, IL-6, IL-8, TNF, COX-2) measured.

Harris' Hematoxylin (Baxter Scientific Products) and Eosin staining were carried out on the formalin-fixed samples using standard procedures. Luna LG: Manual of histological staining methods of the Armed Forces Institute of Pathology, 3$^{rd}$ Ed. NY, McGraw-Hill, 1968. Sections (8 $\mu$m) of each fixed sample of liver were collected on glass slides, de-waxed using xylene, and re-hydrated by passing through graded alcohols. The specimens were stained with hematoxylin and counter stained with eosin (H&E). The slides were then mounted with a xylene miscible mounting medium and cover slipped. The degree of overt tissue necrosis, fatty liver, and inflammation of the H&E stained liver samples was assessed.

6.2.3 Markers of ROS Production

Malondialdehyde and other peroxidation products were measured by determining the amount of thiobarbituric acid reactive products (TBARS) in each sample. Andersen H J et al., 1993, Free Radical Biol. Med. 15:37–48. Briefly, 1 ml of homogenate is mixed with 0.5 ml TCA and centrifuged to pellet the denatured protein. Supernatant (0.5 ml) is then mixed with 0.7% thiobarbituric acid (7% in H$_2$O: acetic acid, 1:1) and boiled for 30 minutes. After cooling the absorbance is read at 532 nm and using a molar extinction coefficient of 153,000 mol$^{-1}$ giving malondialdehyde equivalents.

6.2.4 Markers of Inflammation

The effects of the treatments on the acute phase inflammatory response was determined by measuring concentrations of IL-1, IL-6, TNF, COX-2, & IL-8 in the 16,000× g supernatant of homogenates by a dot-blot procedure and quantified by densitometry essentially as described. Ardies C M et al., 1996, Cancer Letters 103:209–218. Antibodies were purchased from Genzyme and Sigma because their antibodies cross-react with rat cytokines and acute phase proteins. Briefly, protein concentration of each sample was determined in triplicate using Coomassie Brilliant Blue dye as described. Bradford M M, 1975, Anal. Biochem. 72:248–254. Samples were then diluted to 1 mg/ml with phosphate buffered saline (PBS) and 10, 30, and 90 µg of each sample spotted onto a nitrocellulose membrane. After drying at 80° C. for 10 minutes the blots were blocked with 5% dry milk in PBS for 60 minutes, incubated with antibodies which recognized IL-1, IL-6, IL-8, TNF, or COX-2 for 12 hours. After rinsing and re-blocking, the blots were incubated with the secondary antibody which was conjugated to gold (10 nm particles) for 6 hours. The blots were then rinsed and developed in silver-stain to produce black spots where ever the primary antibody recognized the appropriate antigen. With this technique as little as 10 ng of antigen can be visualized.

6.2.5 Mitochondrial Electron Transport Chains

Mitochondria were isolated from the liver essentially as described. Hakvoort, TDM, 1990, Proc. Natl. Acad. Sci. USA 87:4996–5000. Briefly, the livers were homogenized in 10 mM Hepes (pH 7.4) containing 220 mM mannitol, 20 mM sucrose, 10 mM Na succinate, 2.5 mM K2HPO4, 1 mM PMSF, and 1 mM DTT and the homogenate centrifuged at 1000× g to remove cell debris and then the supernate centrifuged at 12,000× g to pellet the mitochondria. The pellet was washed by resuspension in the homogenization buffer and centrifuged again at 12,000× g. The isolated mitochondria resuspended to a final protein concentration of 10 mg/ml. Oxygen uptake was determined in the presence of 10 mM succinate, 1 mM cytochrome c and 0.5% Triton X-100. Under these detergent-disrupted conditions the amount of oxygen consumption is dependant only on the number of electron transport chains per mg of mitochondrial protein.

6.2.6 Statistical Analysis

Because 3 types of toxin treatment (C, X, and E) are used at two levels of protection (none and O) a treatments by protection (3×2) two-factor analysis of variance (ANOVA) was be used to analyze the data.

6.3 Results

Sprague-Dawley rats were treated with methotrexate at a dose of 100 µg/kg body weight in a nutritionally adequate liquid diet. In order to compare ethanol-induced effects to those of methotrexate, ethanol also was given to rats at a dose of 36% of calories in a liquid diet. Orazamide orotate was added to the diets at a dose of 10 mg/kg body weight to determine if orazamide orotate could alter the methotrexate- or ethanol-induced changes. All animals were pair-fed to the amount of food eaten by the ethanol-treated group to ensure similar caloric and nutrient intake because ethanol inhibits food intake. Animals which voluntarily consumed less were allowed to eat the lower amounts because this would indicate a potential drug effect.

Alterations in food consumption, body-weight, liver-weight, kidney-weight, and adrenal-weight over a period of six weeks treatment are presented in FIGS. 1 through 11. As displayed in FIG. 1 the EO treatment resulted in a significant decline in food intake compared to all others while after five weeks treatment the X group started to reduce food intake. In the presence of ethanol, orazamide orotate appears to interact to reduce food intake further than ethanol alone would. In contrast, the X treatment reduced food intake in the last two weeks only while O treatment did not appear to alter food consumption. Over the period of 6 weeks only the XO group displayed a significant reduction in weight-gain (FIG. 4). There appeared to be a trend for X to cause liver hypertrophy with O preventing the increase (FIG. 7) while ethanol produced a significantly enlarged liver and the O did not alter the E-induced liver hypertrophy. There were no effects on kidney with the exception of a significantly enlarged kidney following EO-treatment (FIG. 9). Both E and EO caused significantly enlarged adrenal weights, potentially indicating some type of stress-response.

Samples of liver were fixed in formalin, slides prepared, and examined by a pathologist who observed significant fatty infiltration in both the E and EO groups with a trend for the EO treatment to be less than the E treatment (FIG. 14). There was a protective effect with O on this parameter if the study were continued for a longer time or if different doses were used. There was a trend for O to non-significantly increase fatty deposition in the liver of the control and X groups. Why the orotate appeared to decrease fatty deposits in the liver of the ethanol-treated rats is unknown.

Thiobarbituric Acid Reactive products (an indicator of lipid peroxidation) were determined in the liver homogenates and no differences were observed, indicating that there were no ongoing peroxidative reactions (FIG. 12). One of the major cellular effects of any toxic reaction due to chemical treatment is an influx of calcium which initiates a series of cellular responses, including increased rates of lipid peroxidation.

The effects of the treatments on the number of electron transport chains in hepatic mitochondria are illustrated in FIG. 13. X induced a significant decline in the number of electron transport chains which was prevented by co-administration of O. In contrast, there was a trend for E to reduce this same parameter and for O to enhance the E-induced decline. Because X interferes with DNA synthesis one may expect that rates of protein synthesis to be ultimately affected. Apparently the mitochondria are very sensitive to alterations in protein synthesis and declines in this parameter may be observed before more overt pathological indication are observed. Perhaps the decline observed (and apparent attenuation by O) after 6 weeks treatment is the first step in a slow-progressive toxic reaction which would be apparent in other measures following a longer duration of treatment.

Levels of IL-6, IL-1, IL-8, TNF, and COX-2 were determined in samples of liver and no indications of any treatment-effect at doses used was observed for any of these parameters. These negative results are consistent with the lack of inflammation observed in the pathological examination.

The present invention is not to be limited in scope by the embodiments disclosed in the examples which are intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Various publications are cited herein, the disclosures of which are incorporated by reference in their entireties.

It will thus be seen that the objects set forth above, among those made apparent from the preceding description, are efficiently attained and, since certain changes may be made in carrying out the above method and in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall there between.

What is claimed is:

1. A method of inhibiting tissue damage caused by alcohol in an individual comprising administering to an individual in need thereof a therapeutically effective amount of a composition comprising a salt of 5-aminoimidazole-4-carboxamide.

2. The method according to claim 1, wherein the composition comprises an organic salt derived from a combination of 5-aminoimidazole-4-carboxamide and an acid selected from the group consisting of orotic, lactic, succinic, maleic, citric, tartaric, gluconic and galactonic.

3. The method according to claim 1, wherein the composition comprises an inorganic acid salt derived from a combination of 5-amino-imidazole-4-carboxamide and an acid selected from the group consisting of hydrochloric and phosphoric.

4. The method according to claim 1, wherein the composition is administered orally, intravenously, transcutaneousy or transdermally.

5. A method of inhibiting the oxidation of ethanol said method comprising administration of an effective dose of a salt of 5-aminoimidazole.

6. The method according to claim 1 further comprising antioxidant therapy selected from the group consisting of N-acetylcysteine, vitamin E, vitamin A and its derivatives, vitamin C, gluthathione, cysteine, methionine and 2-mercaptoethanol.

7. A method of inhibiting tissue damage caused by a therapeutic drug in an individual comprising administering to an individual in need thereof a therapeutically effective amount of a composition comprising a salt of 5-aminoimidazole-4-carboxamide.

8. The method according to claim 7, wherein the composition comprises an organic salt derived from a combination of 5-aminoimidazole-4-carboxamide and an acid selected from the group consisting of orotic, lactic, succinic, maleic, citric, tartaric, gluconic and galactonic.

9. The method according to claim 7, wherein the composition comprises an inorganic acid salt derived from a combination of 5-amino-imidazole-4-carboxamide and an acid selected from the group consisting of hydrochloric and phosphoric.

10. The method according to claim 7, wherein the composition is administered orally, intravenously, transcutaneousy or transdermally.

11. A method of inhibiting conversion of therapeutic drugs to reactive metabolites, said method comprising administration of a salt of 5-aminoimidazole.

12. The method according to claim 7 further comprising antioxidant therapy selected from the group consisting of N-acetylcysteine, vitamin E, vitamin A and its derivatives, vitamin C, gluthathione, cysteine, methionine and 2-mercaptoethanol.

13. A method of inhibiting tissue damage caused by a toxin in an individual comprising administering to an individual in need thereof a therapeutically effective amount of a composition comprising a salt of 5-aminoimidazole-4-carboxamide.

14. The method according to claim 13, wherein the composition comprises an organic salt derived from a combination of 5-aminoimidazole-4-carboxamide and an acid selected from the group consisting of orotic, lactic, succinic, maleic, citric, tartaric, gluconic and galactonic.

15. The method according to claim 13, wherein the composition comprises an inorganic acid salt derived from a combination of 5-amino-imidazole-4-carboxamide and an acid selected from the group consisting of hydrochloric and phosphoric.

16. The method according to claim 13, wherein the composition is administered orally, intravenously, transcutaneously or transdermally.

17. A method of detoxifying toxins, said method comprising administration of an effective dose of a salt of 5-aminoimidazole.

18. The method according to claim 13 further comprising antioxidant therapy selected from the group consisting of N-acetylcysteine, vitamin E, vitamin A and its derivatives, vitamin C, gluthathione, cysteine, methionine and 2-mercaptoethanol.

19. A method for preventing suppression of immunity caused by an agent comprising essentially of alcohol, therapeutic drug or a toxin, said method comprising administration of an effective dose of a salt of 5-aminoimidazole carboxamide.

20. The method according to claim 19 further comprising antioxidant therapy selected comprising antioxidant therapy selected from the group consisting of N-acetylcysteine, vitamin E, vitamin A and its derivatives, vitamin C, gluthathione, cysteine, methionine and 2-mercaptoethanol.

* * * * *